(12) United States Patent
Oetting et al.

(10) Patent No.: US 11,544,034 B2
(45) Date of Patent: Jan. 3, 2023

(54) METHOD FOR SETTING PARAMETERS FOR INDIVIDUAL ADAPTATION OF AN AUDIO SIGNAL

(71) Applicant: Fraunhofer-Gesellschaft zur Förderung der angewandten Forschung e.V., Munich (DE)

(72) Inventors: Dirk Oetting, Hatten (DE); Tobias Bruns, Westerstede (DE); Jan Rennies-Hochmuth, Oldenburg (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 16/843,305

(22) Filed: Apr. 8, 2020

(65) Prior Publication Data
US 2020/0233638 A1    Jul. 23, 2020

Related U.S. Application Data

(63) Continuation of application No. PCT/EP2018/077951, filed on Oct. 12, 2018.

(30) Foreign Application Priority Data

Oct. 16, 2017    (DE) ................ 10 2017 218 483.3

(51) Int. Cl.
*G06F 3/16* (2006.01)
*A61B 5/12* (2006.01)
(Continued)

(52) U.S. Cl.
CPC ............. *G06F 3/165* (2013.01); *A61B 5/123* (2013.01); *H03G 5/025* (2013.01); *G01L 9/0079* (2013.01);
(Continued)

(58) Field of Classification Search
CPC ......... G06F 3/165; G06F 3/048; A61B 5/123; H03G 5/025; H03G 5/02; H04R 25/20;
(Continued)

(56) References Cited

U.S. PATENT DOCUMENTS 8,165,327 B2    4/2012    Pape
8,751,934 B2    6/2014    Young
(Continued)

FOREIGN PATENT DOCUMENTS

DE    102006046699    1/2008
EP    2031902 A2    3/2009
(Continued)

OTHER PUBLICATIONS

The British Society of Audiology: Recommended Procedure, Pure tone air and bone conduction threshold audiometry with and without masking, 2011-2015.
(Continued)

*Primary Examiner* — Matthew A Eason
*Assistant Examiner* — Kuassi A Ganmavo
(74) *Attorney, Agent, or Firm* — Perkins Coie LLP; Michael A. Glenn (57) ABSTRACT

Method for setting parameters for individual adaptation of an audio signal, including: performing a first listening test with the substeps:
 playing a plurality of first audio signals having different levels;
 obtaining feedback per frequency range from an individual which of the plurality of first acoustic signals is above an individual listening threshold; and
 using the lowest level of the different levels for which feedback is available as a level for the individual listening threshold per frequency range;
performing adaptation of a second audio signal with the substeps:
(Continued)

playing the second audio signal according to a total volume level considering a sound adaptation characteristic map; and varying the sound adaptation characteristic wherein the levels for the individual listening thresholds are used as minimum output levels in the sound adaptation characteristic map.

15 Claims, 5 Drawing Sheets

(51) Int. Cl.
    *H03G 5/02*     (2006.01)
    *G01L 9/00*     (2006.01)
    *H04R 25/00*     (2006.01)
    *G06F 3/048*     (2013.01)

(52) U.S. Cl.
    CPC .............. *G06F 3/048* (2013.01); *H03G 5/02* (2013.01); *H04R 25/505* (2013.01); *H04R 25/554* (2013.01); *H04R 25/70* (2013.01)

(58) Field of Classification Search
    CPC .... H04R 25/554; H04R 25/70; H04R 25/505; G01L 9/0079
    See application file for complete search history.

(56) References Cited

U.S. PATENT DOCUMENTS

| | | | |
|---|---|---|---|
| 8,964,998 B1 | 2/2015 | McClain | |
| 9,445,169 B2 | 9/2016 | Appell et al. | |
| 2002/0172350 A1* | 11/2002 | Edwards | G10L 21/02 379/392.01 |
| 2004/0234089 A1 | 11/2004 | Rembrand et al. | |
| 2007/0121979 A1* | 5/2007 | Zhu | H04R 25/505 381/315 |
| 2008/0008070 A1* | 1/2008 | Kwon | H03G 5/165 369/53.1 |
| 2008/0130928 A1 | 6/2008 | Barthel et al. | |
| 2009/0164905 A1* | 6/2009 | Ko | H04M 1/6016 715/727 |
| 2009/0232329 A1* | 9/2009 | Kwon | H03G 3/002 381/103 |
| 2010/0232747 A1* | 9/2010 | Duis | G02B 6/3809 385/78 |
| 2010/0235747 A1 | 9/2010 | Young | |
| 2011/0200217 A1* | 8/2011 | Gurin | A61B 5/123 381/320 |
| 2013/0102362 A1* | 4/2013 | Inagaki | H04M 1/60 455/563 |
| 2013/0339025 A1* | 12/2013 | Suhami | H04R 3/569 704/271 |
| 2014/0079243 A1* | 3/2014 | Appell | H03G 3/32 381/86 |
| 2014/0161272 A1* | 6/2014 | Marquis | G10L 21/0208 381/71.7 |
| 2014/0194775 A1 | 7/2014 | Van Hasselt et al. | |
| 2014/0334642 A1* | 11/2014 | Kwak | H03G 9/025 381/102 |
| 2016/0050507 A1* | 2/2016 | Moore | G06F 3/162 381/57 |
| 2016/0277855 A1 | 9/2016 | Raz | |

FOREIGN PATENT DOCUMENTS

| | | |
|---|---|---|
| JP | H05206772 A | 8/1993 |
| JP | H10341123 A | 12/1998 |
| JP | 2001156568 A | 6/2001 |
| JP | 2002281599 A | 9/2002 |
| JP | 2009077378 A | 4/2009 |
| JP | 2010277617 A | 12/2010 |
| JP | 2010278791 A | 12/2010 |
| JP | 2012213114 A | 11/2012 |
| JP | 5206772 B2 | 3/2013 |
| JP | 2013247559 A | 12/2013 |
| JP | 2015510707 A | 4/2015 |
| JP | 5898305 B2 | 3/2016 |
| JP | 2016511648 A | 4/2016 |
| WO | 2006044644 A2 | 4/2006 |

OTHER PUBLICATIONS

Christoph, Markus, "Noise dependent equalization control", Audio Engineering Society Conference: 48th International Conference: Automotive Audio. Audio Engineering Society, 2012.

* cited by examiner

METHOD FOR SETTING PARAMETERS FOR INDIVIDUAL ADAPTATION OF AN AUDIO SIGNAL

CROSS-REFERENCE TO RELATED APPLICATIONS

This application is a continuation of copending International Application No. PCT/EP2018/077951, filed Oct. 12, 2018, which is incorporated herein by reference in its entirety, and additionally claims priority from German Application No. EP 10 2017 218 483.3, filed Oct. 16, 2017, which is also incorporated herein by reference in its entirety.

Embodiments of the present invention relate to a method as well as an apparatus for setting parameters by means of which an audio signal can be adapted individually. A further embodiment relates to a computer program. Embodiments relate to the individual sound adaptation by considering the effective listening threshold.

BACKGROUND OF THE INVENTION

For adapting music signals to individual hearing, adaptation of an equalizer is a widely known variation in current audio devices. By an equalizer, frequency-dependent amplification can be applied to the music signal before the same is played. However, operating an equalizer is frequently complicated for a non-professional, since currently only individual frequency bands can be changed. Therefore, in the past, methods have been developed to adapt the sound to the hearing in a simplified or guided method. Here, different aspects having an influence on the perceived sound have to be considered: the acoustic path from loudspeaker/headphones to the ear, the technical limits for the maximum acoustic level, background noise, possible limitation of the hearing ability as well as the spectral content of the piece of music for which the adaptation is to be made. For compensating the hearing ability, some methods use measurement methods to determine the individual listening threshold. Recent studies show that the sound setting when listening to music cannot be inferred based on the listening threshold, i.e., persons with the same frequency-dependent listening threshold can have very different sound preferences. Listening to music at normal volume (i.e. above the listening threshold) is determined by the absolute listening threshold only to a very limited extent. Further, the sound preferences differ between different pieces of music such that there is not "the" optimum equalizer setting for different pieces of music.

Some existing methods try to estimate the listening threshold of the user (e.g. Mimi Music app, Samsung Sound Adapt) and to thereby set the parameters for sound personalization (here, the same sound setting follows from the same listening threshold). One problem here is that the listening threshold measurement is performed on non-calibrated audio devices. The used headphone, and hence the transmission path of the system, are unknown. Thus, no absolute listening threshold measurement as with a calibrated audiometer can be made.

The settings in hearing aids are made based on the measured listening threshold, but the adaptation is made by an expert (audiologist). The user of the hearing aid can switch between predetermined programs, but cannot perform any free change of the sound parameters.

In adaptation methods that do not determine the listening thresholds, default settings for the sound parameters are provided to the user on a user interface, by which the user can set the sound of the current signal (e.g. Soundhawk app, EARs, Earmachine, BioAid). However, these adaptation concepts do not consider the individual listening threshold of the user, which plays a role in quiet passages of a piece of music.

For sound adaptation in cars, a system has been presented (cf. Christoph, Markus. "Noise dependent equalization control." Audio Engineering Society Conference: 48th International Conference: Automotive Audio. Audio Engineering Society, 2012), which applies, for a given background noise, frequency-dependent amplification to the target signal such that the sound impression is maintained for variable background noise. However, this solution does not consider individual differences of the listener, which exist, for example, based on the individual hearing ability.

Methods for automotive audio systems have been patented ("Sound reproduction device including auditory scenario simulation"; e. g. U.S. Pat. No. 9,445,169 or JP 5898305) that play simulated driving/ambient noise to the user, while he/she implements the individual sound settings (training phase) and then analyze the real driving/ambient noise during the operating phase and automatically select those sound settings for which the simulated ambient noise is most likely to match the real noise. Therefore, there is a need for an improved approach.

SUMMARY

According to an embodiment, a method for setting parameters for individual adaptation of an audio signal may have the steps of: performing a first listening test with the following substeps: playing a plurality of first audio signals with different levels and for different frequency ranges to output a plurality of first acoustic signals of different sound pressure levels in the different frequency ranges to an individual; obtaining feedback per frequency range of the different frequency ranges from the individual, which of the plurality of first acoustic signals is above an individual listening threshold; and using, per frequency range of the different frequency ranges, the lowest level of the different levels of the plurality of first audio signals for which feedback is available, which characterizes the associated first acoustic audio signal as an acoustic audio signal above the individual listening threshold, as a level for the individual listening threshold per frequency range of the different frequency ranges; performing adaptation of a second audio signal with the following substeps: playing the second audio signal according to a total volume level selected by the individual considering a sound adaptation characteristic map to output a post-processed second acoustic signal to the individual; and varying the sound adaptation characteristic map by means of a user interface or a control until the individual indicates by interaction that no further variation of the sound adaptation characteristic map is desired; wherein the sound adaptation characteristic map defines an individual boost and/or individual cut of the output level per input level for different frequency ranges, wherein the levels for the individual listening thresholds per frequency range of the different frequency ranges are used as minimum output levels in the sound adaptation characteristic map.

Another embodiment may have a non-transitory digital storage medium having a computer program stored thereon to perform the inventive method for setting parameters for individual adaptation of an audio signal when said computer program is run by a computer.

According to another embodiment, an apparatus for setting parameters for individual adaptation of an audio signal may have: an initial adaptation stage for defining levels for an individual listening threshold per frequency range of the different frequency ranges, having means for: playing a plurality of first audio signals having different levels and for different frequency ranges to output a plurality of first acoustic signals of different sound pressure levels in the different frequency ranges to an individual; obtaining feedback per frequency range of the different frequency ranges from the individual, which of the plurality of first acoustic signals is above the individual listening threshold; and wherein, per frequency range of the different frequency ranges, the lowest level of the different levels of the plurality of first audio signals for which feedback is available, which characterizes the associated first acoustic audio signal as an acoustic audio signal above the individual listening threshold, is used as the level for the individual listening thresholds per frequency range of the different frequency ranges; a further adaptation stage for adapting a second audio signal, having means for: playing the second audio signal according to a total volume level selected by the individual considering a sound adaptation characteristic map to output a post-processed second acoustic signal to the individual; and varying the sound adaptation characteristic map by means of a user interface or a control until the individual indicates by interaction that no further variation of the sound adaptation characteristic map is desired; wherein the sound adaptation characteristic map defines an individual boost and/or individual cut of the output levels per input level for different frequency ranges; wherein the levels for the individual listening thresholds per frequency range of the different frequency ranges are used as minimum output levels in the sound adaptation characteristic map.

Embodiments of the present invention provide a method for setting parameters for individual adaptation of an audio signal. This setting method is divided into two phases: in the first phase, some sort of listening test is performed, with the aim of obtaining a level adapted to the individual listening threshold (per frequency range). This first phase is performed with the help of a first audio signal, such as a test signal or also a real signal. In the second phase, the second (e.g. actual) audio signal is set by varying a sound adaptation characteristic map by considering the level for the individual listening thresholds per frequency range. In detail: the method includes the steps of performing a first listening test and performing adaptation of the second audio signal. The first listening test includes the following substeps:

playing a plurality of first audio signals with different levels and for different frequency ranges to output a plurality of first acoustic signals of different sound pressure levels in the different frequency ranges to an individual;

obtaining feedback per frequency range of the different frequency ranges from the individual, which of the plurality of the first acoustic signals is above an individual listening threshold; and using, per frequency range of the different frequency ranges, the lowest level of the different levels of the plurality of the first audio signals for which feedback is available, which characterizes the associated first acoustic audio signal as an acoustic audio signal above the individual listening threshold, as a level for the individual listening threshold per frequency range of the different frequency ranges.

Based on the frequency-dependent levels for the individual (frequency-dependent) listening threshold determined in that way, adaptation is performed with the following substeps:

playing the second audio signal according to a total volume level selected by the individual by considering a sound adaptation characteristic map to output a post-processed second acoustic signal to the individual;

varying the sound adaptation characteristic map until the individual indicates by interaction that no further variation of the sound adaption characteristic map is desired.

Here, the sound adaptation characteristic map defines an individual boost and/or individual cut of the output levels per input level for different frequency ranges. The levels for the individual listening thresholds per frequency range of the different frequency ranges are used as minimum output levels in the sound adaptation characteristic map. In that way, the levels for the individual listening thresholds (per frequency range) are also stored in the sound adaptation characteristic maps.

According to the embodiment, storing is performed such that this sound adaptation characteristic map can be used for replaying the second audio signal, i.e. for example, the audio signal to be currently played. According to a further embodiment, the step of adapting can be repeated at a later time, for example when a variation of the audio signal is desired. According to embodiments, this step is referred to as a sound adaptation online or readjustment of the current signal and still considers the levels for the individual listening thresholds per frequency range determined in the first listening test.

Embodiments of the present invention are based on the knowledge that individual sound adaptation can be obtained by considering the effective listening thresholds by a two-phase method. In the first phase, an (offline) listening test is performed for estimating the effective listening threshold, while in the second phase a method for sound adaptation of music signals is performed (offline or online). Optionally, this approach can be extended by a third phase for readjustment of the current signal, wherein this third phase essentially repeats the steps of the second phase in order to modify the sound characteristic "online" (i.e. during operation). For this, the first phase does not have to be repeated, since the effective listening threshold is person-related (and represents an invariable listening characteristic from the view of the respective person) and usually does not have to be redetermined.

Estimating the effective listening threshold in the first phase has the effect of determining the lower limit for signal presentation. This means that the sound adaptation characteristic map is defined such in the subsequent application of the same to the audio signal to be played, quiet signal portions in the entire frequency range remain audible, i.e. above the individual effective listening threshold. Sound personalization is performed by a selection of compression settings selected by the user, wherein the user can vary live between different sound adaptations while listening (phase 3) according to further embodiments. In this phase 2 or in the repeated phase 2, i.e. phase 3, sound adaptations are performed at middle and high signal levels.

From another point of view, this means that the sound adaptation characteristic map including, of the first phase, at least the levels for the individual listening thresholds (minimum levels) by which the respective (output) level adaptations are extended middle and high signal levels (input level). Here, it is obvious that both the individual listening thresholds are defined in different frequency ranges as well as the level boosts/cuts for the middle and high signal level are varied in a frequency-selective manner. The most important advantage is the consideration of the individual sound preference and the individual effective listening threshold within a sound setting. The effective listening threshold ensures that quiet signal portions remain audible. In a middle to high volume range, the effective listening threshold only plays a minor part. Thus, here, the settings of sound preference are used. This method combines considering the effective individual listening threshold and individual sound adaptation for listening to music under real listening conditions.

According to embodiments, the listening test and the adaptation are performed by using the audio devices selected by the individual and/or in the acoustic environment of the individual. This has the advantage that no specifically calibrated device is needed and device-specific characteristics are directly considered as well. Further, characteristics influenced by the listening room or the position of the individual in the listening room and here, in particular, the distance and the associated attenuation of the volume level are also considered. This approach also has the advantage that the concept is not restricted to a specific hardware and that the complete listening situation is considered. When the listening situation changes, the method can be performed again. According to further embodiments, it should also be noted that the first audio signal for determining the individual listening threshold can include a signal portion allowing simulation of driving and/or ambient noise.

According to further embodiments, in particular the step of adapting the second audio signal is repeated for different total volume levels (i.e. for different output volume levels selected by the user). This enables that the sound adaptation characteristic map is stored per total volume level. After successful implementation, the volume control of the audio system is calibrated to the individual listening situation, such that the signal only falls below the listening threshold and thereby becomes inaudible at the lowest stage of the control. The maximum volume setting uses the entire dynamic range of the technical system.

Particularly in the third phase or when performing the second phase, it would be desirable that adaptation is performed continuously. Thus, varying the sound adaptation characteristic map is performed by continuously adapting at least one dimension of the sound adaptation characteristic map in order to smooth the resulting sound characteristic variation over time and/or the sound pressure level differences over time. This adaptation is typically performed by interaction with the user actuating a control, such as, for example, a two-dimensional shift control or three individual controls for bass, middle and treble. With a similar control, interaction takes place between user and executing apparatus when determining the effective listening threshold. Here, it should be noted that the signal for determining the effective listening threshold can, for example, be a test signal, while the second audio signal can either be a test signal or a complex audio signal (with or without limited frequency range) or also a current piece of music.

According to embodiments, varying the sound adaptation characteristic map is performed for input values above the level for the individual listening threshold and for levels below a level for limitation. Here, according to further embodiments, input levels of at least 10 dB above the respective level for the individual listening threshold and/or levels of at least 3 dB below the respective level for limitation can be varied. This level range is particularly interesting since the same determines the sound characteristic. According to further embodiments, the variation of the sound adaptation characteristic map is such that the same does not fall below a masking threshold, wherein the masking threshold depends on the individual listening threshold.

Adapting or applying the sound adaptation characteristic map is performed with the help of a multiband compressor that is configured to post-process the second audio signal in dependence on the sound adaptation map with respect to the output levels in the different frequency ranges.

A further embodiment relates to a computer program for performing one of the above-discussed methods.

A further embodiment relates to an apparatus that can perform setting of parameters for individual adaptation of the audio signal. This apparatus includes an additional adaptation stage with means for performing the substeps of the listening tests as well as a further adaptation stage for adapting the second audio signal with means for performing the substeps of adapting.

BRIEF DESCRIPTION OF THE DRAWINGS

Embodiments of the present invention will be detailed subsequently referring to the appended drawings, in which.

DETAILED DESCRIPTION OF THE INVENTION

Before embodiments of the present invention will be discussed below with reference to the figures, it should be noted that the same elements and structures are provided with the same reference numbers such that the description of the same is inter-applicable or inter-exchangeable.

Figure 1A:
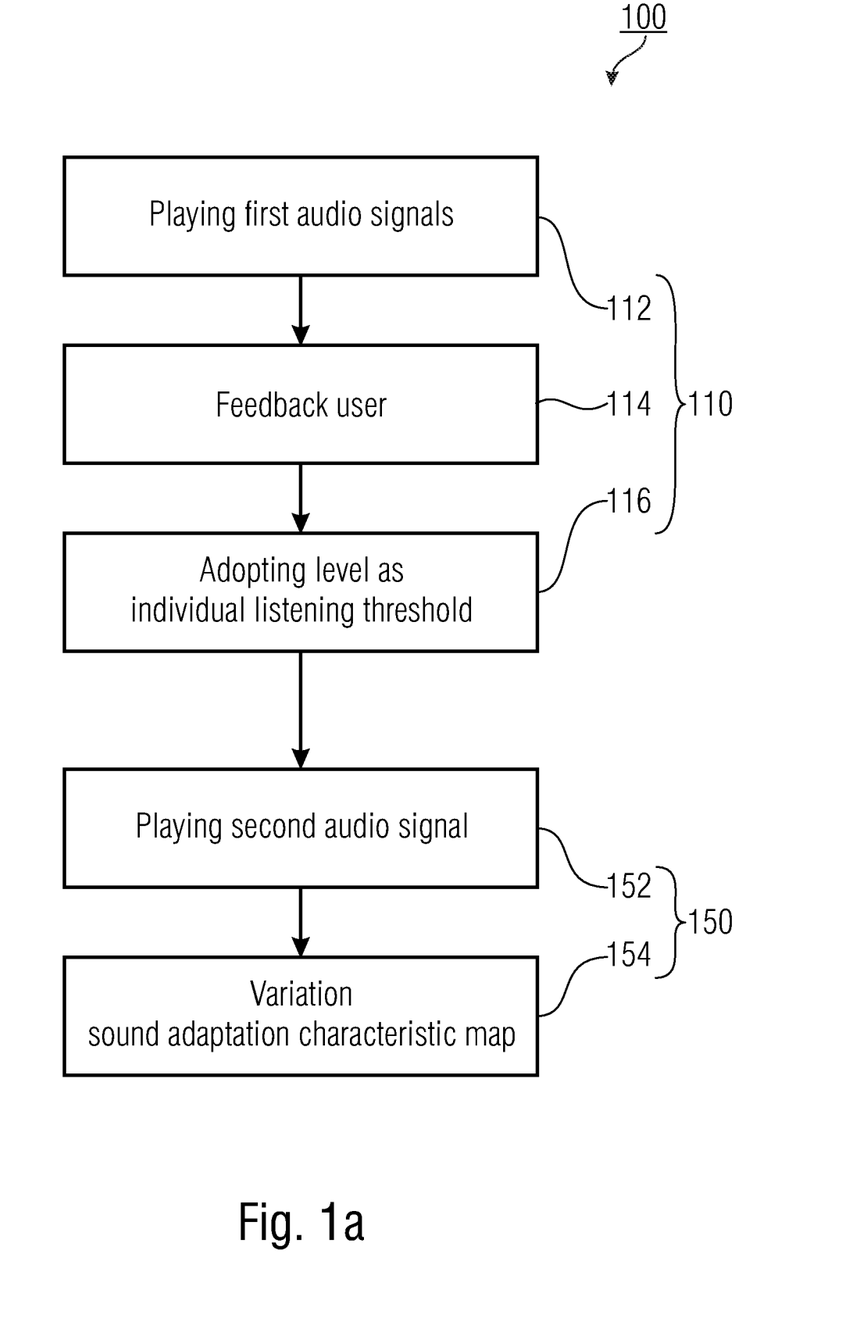
FIG. 1a is a schematic flow diagram of a method for setting parameters for individual adaptation according to an embodiment.

FIG. 1a shows a method 100 with two phases 110 and 150. In the first phase 110, a first listening test is performed with the aim of determining levels for individual listening thresholds per frequency range (with respect to different frequency ranges). The phase 150 serves for the adaptation and has the aim of obtaining a sound adaptation characteristic map for sound personalization considering the predetermined individual listening thresholds.

In phase 110, essentially, the following three steps 112, 114 and 116 are performed. In step 112, a first audio signal having different levels, e.g. decreasing levels, is played. This first audio signal is played for different frequency ranges to output the first acoustic signal with different switching levels in the different frequency ranges to the individual. The individual hears that and then provides feedback per frequency range in step 114. The feedback characterizes the smallest or generally the first acoustic signals above an individual listening threshold. For example, the user/individual can acknowledge obtaining the first acoustic signal until he or she no longer hears it. The lowest level per frequency range used for this, for which feedback is available, that the associated acoustic signal is above the individual listening threshold is adopted as level for the individual listening threshold per frequency range, as is symbolized by step 116, since the individual listening threshold is frequency-selective, this first listening test is repeated for different frequency ranges, e.g. a high and a low frequency range or a plurality of different frequency ranges (20 to 100 Hz, 100 to 400 Hz, 400 to 4,000 Hz, 4,000 to 10,000 Hz, 10,000 to 20,000 Hz). For example, a specifically prepared music signal (e.g. a band-limited music signal) can be used as first audio signal, such that an effective listening threshold for music signals is determined that can deviate from the audiometric listening threshold measured with sinusoidal tones.

Figure 1B:
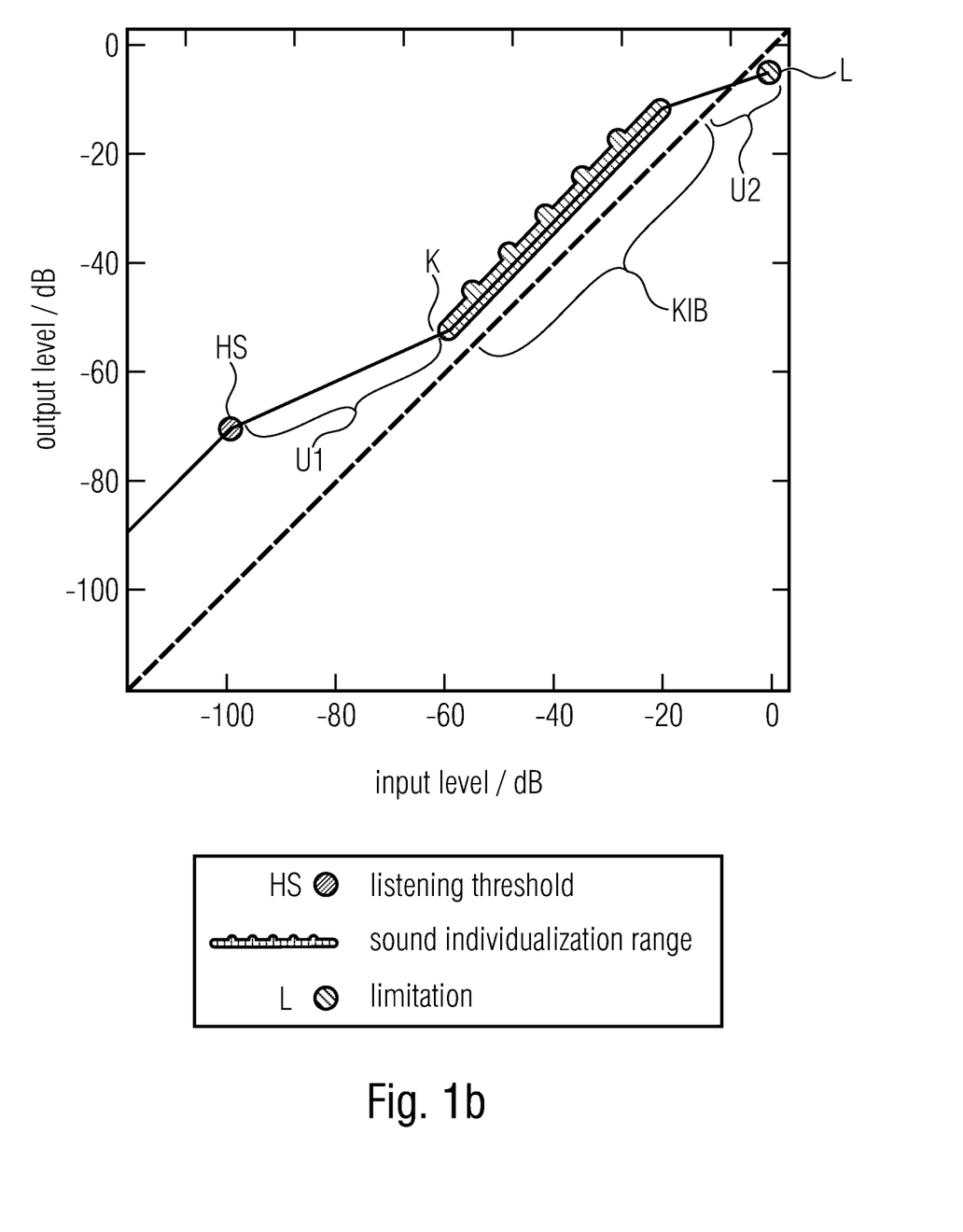
FIG. 1b is a schematic illustration of a compression characteristic curve in a band for illustrating the parameters for individual adaptation according to embodiments.

The result of phase 110 will subsequently be discussed based on FIG. 1b. FIG. 1b shows a diagram of the output level compared to the input levels. In a linear preamplification, an input level is mapped 1 to 1 to an output level. If, for example, −100 dB is assumed, without sound adaptation, a −100 dB signal is output. However, such a signal is below the listening threshold, which is indicated by reference number HS. This listening threshold HS, in this embodiment having about −70 dB, is person-specific and frequency-specific. In that way, this diagram is only valid for one frequency range and also only for one person.

Starting from this determined listening threshold, the signals associated to the lower input levels are increased, such that the output levels based on input levels in the range between −100 dB and −70 dB or in the range between −100 dB and −60 dB are above the listening threshold HS.

In the second phase 150, a second audio signal is adapted. This sound adaptation relates to the middle and high signal levels across the entire frequency range, wherein here adaptation also is performed across different frequency ranges of the entire frequency spectrum. Here, the frequency ranges can be subdivided into one of the frequency bands, analogously to the adaptation in phase 110, or also independent thereof.

The phase 150 includes two steps 152 and 154. Step 152 relates to playing a second audio signal, such as a current music signal corresponding to the total volume level selected by the individual. This is important since the sound preferences are frequently different for the listener in different volume ranges, such that in particular the adaptations determined by means of phase 150 are applied in a total volume level range. The reason for that is that a user might prefer a bathtub curve at a low overall volume (boosted bass and treble), while the same user may tend to a linear amplification with a higher overall volume, such that bass and treble are not boosted to an unpleasant output level range. Further, it should be noted that this second audio signal is played by considering a sound adaptation characteristic map in order to output a second audio signal post-processed in dependence on this sound adaptation characteristic map. FIG. 1b shows a section of the sound adaptation characteristic map, namely the characteristic line K in a specific frequency range, e.g. a range around 100 Hz (800-1500 Hz). The entire sound adaptation characteristic map across all relevant/audible frequencies (30 Hz to 20 kHz or 20 Hz to 22 kHz) is illustrated in FIG. 1c.

Figure 1C:
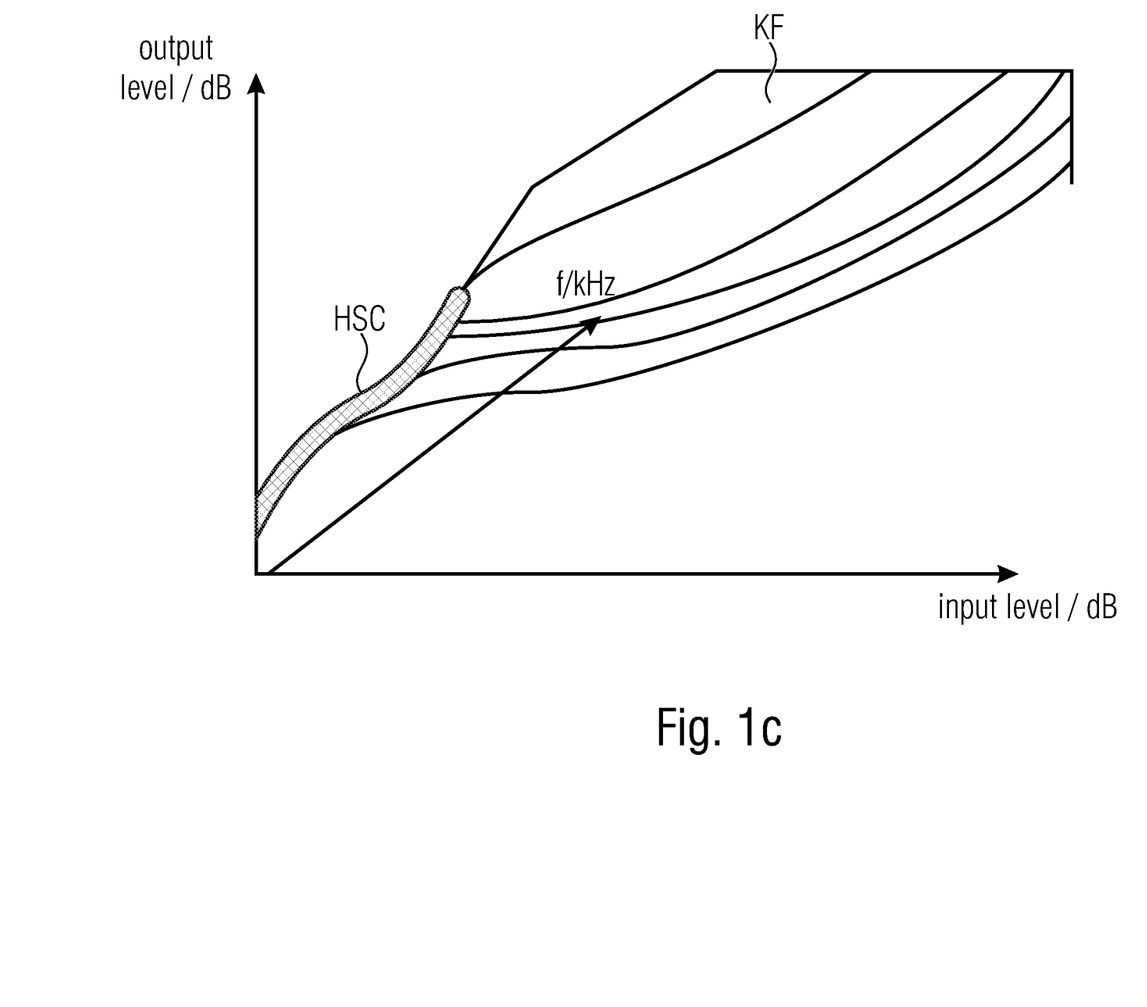
FIG. 1c is a schematic illustration of a three-dimensional sound adaptation characteristic map according to an embodiment.

As can be seen based on FIG. 1c, the sound adaptation characteristic map includes three dimensions, namely, as already shown in FIG. 1b, mapping of input levels compared to output levels and in the third dimension the frequency range in kHz. Even when it is not illustrated, it should be noted here that this sound adaptation characteristic map can also be extended by a fourth dimension, namely the overall volume level.

In step 154, the user varies the sound adaptation characteristic map KF, for example by boosting bass, middle or treble. By this variation, the post-processing of the second acoustic signal changes, such that the user receives direct feedback. However, it is still considered that the same does not fall below individual listening thresholds indicated by reference number HSL when varying the sound adaptation map and that the sound adaptation characteristic map is therefore limited to one region by the line HSL. In the following, with reference to FIG. 1b, the variation 154 will be discussed. This compression characteristic curve K illustrated in FIG. 1b for a band of the compressor can be varied in the so-called sound individualization range KIB between the two black dots. This sound individualization range is typically between the so-called limitation point L and the listening threshold HS, wherein, according to an embodiment, a specific distance, such as 10 dB to HS and 3 dB to L exists. As can be seen, the sound individualization range is therefore disposed in the top range. The bottom range is determined or dominated by the listening threshold HS determined by means of the listening test. Starting from this listening threshold, a transition to the bottom point of the sound individualization range in the range U1 takes place, which shifts in dependence on the points HS and the sound individualization range KIB. When a user desires, for example, a boost of the frequency range within this frequency range, the sound individualization range KIB is either partially or completely shifted towards the top, while a shift towards the bottom takes place when cutting the levels in this frequency range is desired. As already indicated, according to embodiments, the range KIB can be shifted as linear element (no compression) or the range KIB can also be divided into different other ranges. Starting from the shift of this middle range within the sound adaptation, frequency weighting set by the user is performed. Depending on the shift of KIB, the range U2 is adapted, such that a transition up to the limitation L takes place.

Regarding the diagram, it should be noted that the distance of the sound individualization range KIB from the diagonal (dotted line) illustrates whether a boost or cut of the output level with respect to the input level takes place. In the embodiment illustrated herein, there is a boost, apart from the range between an input level of −10 to 0 dB (limitation).

Starting from the compression characteristic curve set in that way, the second audio signal is post-processed, for example as follows: if the presentation level is close to the listening threshold HS, the effective listening threshold determines the processing. If the presentation level is significantly above the threshold HS, sound personalization in the range KIB determines the processing. When reducing the listening volume, this method allows that all signal portions remain in the audible range and no individual frequency ranges fall below the listening threshold. In the middle to high volume range, the individual sound preference dominates the setting of signal processing.

Figure 2:
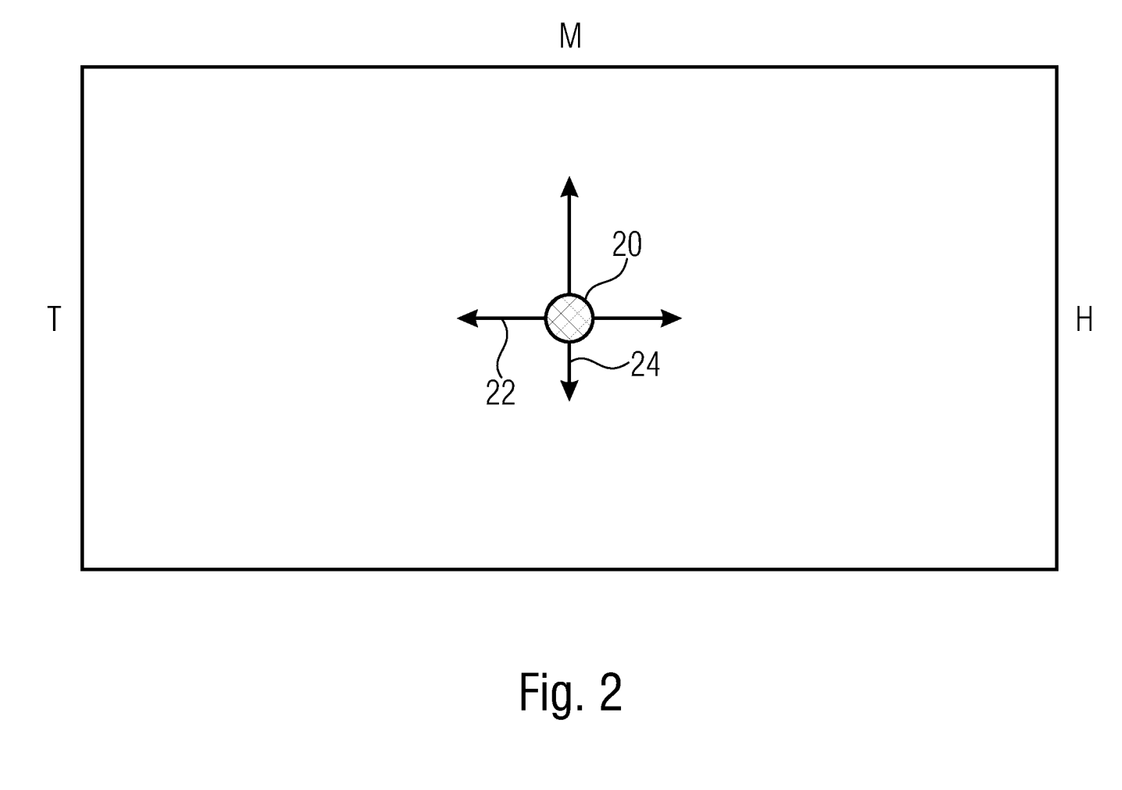
FIG. 2 is a schematic illustration of the individualization stages in a method for individual adaptation according to embodiments.

This adaptation is performed across several frequency ranges, so that the characteristic map KF is obtained as a result. FIG. 2 shows a possible control for the phase of adaptation. Here, a two-dimensional map is assumed which allows, in a first dimension (cf. arrow 22), that sound adaptation takes place more in the direction of bass or more in the direction of treble, depending on whether the setting point 20 is moved in a direction T (bass) or in the direction H (treble). Moving 20 in the direction T results in a boost of the range KIB for a low-frequency frequency band (e.g. in the frequency band between 20 and 150 Hz). Movement in the direction H reduces, on the one hand, the range KIB in the low-frequency frequency band and increases, on the other hand, the boost by KIB in a high-frequency frequency band (e.g. the range between 1,000 and 20,000 Hz). In order to boost the middle range between 150 and 1,000 Hz, point 20 is shifted along the axis 24 in the direction M (middle) which results in a boost of KIB for the middle frequency band.

In order to control treble and bass independent of one another, instead of the control illustrated herein, a control similar to an equalizer, i.e. an arrangement of three controls for T, M and H can be provided independent of one another.

All controls allow the variations of the sound adaptation characteristic map as described with reference to step 154.

Since possibly several characteristic curves for several volume levels (total volume level) are useful, according to further embodiments, the sound adaptation characteristic maps, which are then associated with different overall volume levels, can be stored. Also, storage of different sound adaptation characteristic maps can be provided for different signals (e.g. a speech signal and a music signal) or for different musical styles (classic versus pop) can be stored.

Figure 3:
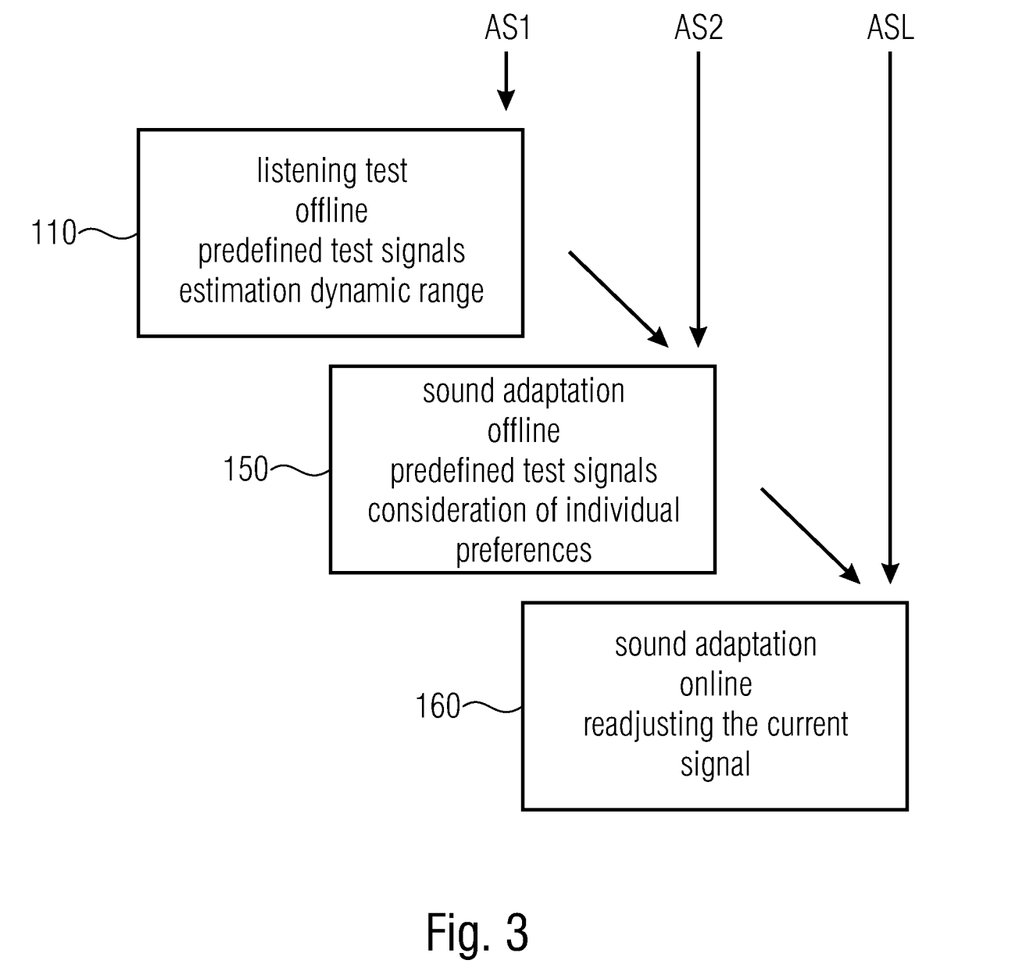
FIG. 3 is a schematic illustration of a user interface for adapting an audio signal according to further embodiments.

According to further embodiments, this phase 150 can be repeated, as illustrated below with reference to FIG. 3. FIG. 3 illustrates the two phases 110, 150 as well as an associated further phase 160 where readjustment of the current signal (current music signal ASL as second audio signal) takes place. Phase 160 can essentially be compared to phase 150, wherein the difference is that a current music signal ASL is used unlike in phase 150 where the sound adaptation takes place offline with the help of predefined test signals (AS2). This phase 160 can also be referred to as a so-called life adaptation. With reference to phase 110, it should be noted that here also a test signal (cf. reference no. AS1) is used.

According to further embodiments, both phase 110 as well as phase 150 and (obviously) phase 160 takes place with the actual acoustic path, such that the influence of background noise and the individual listening capability of the user are considered when determining the sound adaptation characteristic map.

In the context of the embodiments of FIGS. 1b and 1c, it should be noted that the respectively divided frequency range can also influence each other. Here, for example, one frequency range is masked when the other frequency range is extremely boosted compared to the other frequency range. Therefore, according to embodiments, by estimating masking thresholds it can be determined which signal portions are above the listening threshold HS but are not audible due to masking of adjacent bands. In these frequency portions, the listening threshold can be reduced or vice versa the masking bands can be boosted so that these portions remain masked and, hence, inaudible after processing.

A further embodiment relates to an apparatus applying the method 100. Apart from test signal sources and means for feedback input, this apparatus also includes means for sound adaptation. These means for sound adaptation can, for example, be a so-called multiband dynamic compressor configured to perform sound adaptation according to the sound adaptation characteristic map.

In the above stated embodiments, it has been assumed that the entire frequency range is divided into three partial ranges (bass, middle and treble). Obviously, in that way a division into significantly more partial ranges, e.g. in octave steps or comparable, is possible.

With reference to the embodiment of FIG. 3c, it should be noted that for phases 110 and 150, the acoustic path under real conditions is used. If, for example, a car radio is assumed, the real conditions are fulfilled when, for example, ambient noise, e.g. sound noises exist. For still performing adaptation in a stationary situation, according to further embodiments, a simulation of listening scenarios of the listening test 110 or during the sound adaptation 150 can take place. Here, in addition to the actually predefined listening signals, a simulation signal such as ambient noise or driving noise is mixed in with a test signal, such that this ambient noise can be integrated in the measurement or the estimation of the effective listening threshold and the adaptation. Here, it is an advantage that the sound setting during replay operation of the audio system takes place under realistic environmental conditions and in that way it is ensured that neither the individual listening threshold nor existing ambient noise reduces the audibility at low listening volumes.

All above discussed embodiments have in common that both interaction with the user exists for determining the effective listening threshold of the user, as well as interaction of the user to adapt the audio signal above the listening threshold. Both these subjective measurement results with the help of the individual are then considered in signal processing, such that during sound setting at low listening volumes an individual influence, in particular of the individual listening thresholds is provided, while other settings (e.g. EQ) at middle and high listening volumes depend on the listening threshold. With reference to FIG. 1b, there is a transition range U1 between the listening threshold HS and the sound individualization range KIB which is influenced both by the listening threshold and the KIB.

The above-discussed method can be implemented on all devices suitable for replaying audio signals, such as for listening to music. In particular, listening to music in the car is an essential field of application since here time-variable background noise exists and there are large individual sound preferences when listening to music. The usage of radio and TV at home, listening to music in an airplane and on MP3 players and smartphones are further fields of application.

Although some aspects have been described in the context of an apparatus, it is obvious that these aspects also represent a description of the corresponding method, such that a block or device of an apparatus also corresponds to a respective method step or a feature of a method step. Analogously, aspects described in the context of a method step also represent a description of a corresponding block or detail or feature of a corresponding apparatus. Some or all of the method steps may be performed by a hardware apparatus (or using a hardware apparatus), such as a microprocessor, a programmable computer or an electronic circuit. In some embodiments, some or several of the most important method steps may be performed by such an apparatus.

Depending on certain implementation requirements, embodiments of the invention can be implemented in hardware or in software. The implementation can be performed using a digital storage medium, for example a floppy disk, a DVD, a Blu-Ray disc, a CD, an ROM, a PROM, an EPROM, an EEPROM or a FLASH memory, a hard drive or another magnetic or optical memory having electronically readable control signals stored thereon, which cooperate or are capable of cooperating with a programmable computer system such that the respective method is performed. Therefore, the digital storage medium may be computer readable.

Some embodiments according to the invention include a data carrier comprising electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer.

The program code may, for example, be stored on a machine readable carrier.

Other embodiments comprise the computer program for performing one of the methods described herein, wherein the computer program is stored on a machine readable carrier.

In other words, an embodiment of the inventive method is, therefore, a computer program comprising a program code for performing one of the methods described herein, when the computer program runs on a computer.

A further embodiment of the inventive method is, therefore, a data carrier (or a digital storage medium or a computer-readable medium) comprising, recorded thereon, the computer program for performing one of the methods described herein.

A further embodiment of the inventive method is, therefore, a data stream or a sequence of signals representing the computer program for performing one of the methods described herein. The data stream or the sequence of signals may, for example, be configured to be transferred via a data communication connection, for example via the Internet.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment in accordance with the invention includes an apparatus or a system configured to transmit a computer program for performing at least one of the methods described herein to a receiver. The transmission may be electronic or optical, for example. The receiver may be a computer, a mobile device, a memory device or a similar device, for example. The apparatus or the system may include a file server for transmitting the computer program to the receiver, for example.

In some embodiments, a programmable logic device (for example a field programmable gate array, FPGA) may be used to perform some or all of the functionalities of the methods described herein. In some embodiments, a field programmable gate array may cooperate with a microprocessor in order to perform one of the methods described herein. Generally, the methods are performed by any hardware apparatus. This can be a universally applicable hardware, such as a computer processor (CPU) or hardware specific for the method, such as ASIC.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. Method for setting parameters for individual adaptation of an audio signal, comprising:
   performing a first listening test with the following substeps:
      playing a plurality of first audio signals with different levels and for different frequency ranges to output a plurality of first acoustic signals of different sound pressure levels in the different frequency ranges to an individual;
      obtaining feedback per frequency range of the different frequency ranges from the individual, which of the plurality of first acoustic signals is above an individual listening threshold; and
      using, per frequency range of the different frequency ranges, the lowest level of the different levels of the plurality of first audio signals for which feedback is available, which characterizes the associated first acoustic audio signal as an acoustic audio signal above the individual listening threshold, as a level for the individual listening threshold per frequency range of the different frequency ranges;
   performing adaptation of a second audio signal with the following substeps:
      playing the second audio signal according to a total volume level selected by the individual considering a sound adaptation characteristic map to output a post-processed second acoustic signal to the individual; and
      varying the sound adaptation characteristic map by means of a user interface or a control until the individual indicates by interaction that no further variation of the sound adaptation characteristic map is desired;
   wherein the sound adaptation characteristic map defines an individual boost and/or individual cut of the output level per input level for different frequency ranges, wherein the varying the sound adaptation characteristic map is performed based on an interaction of the individual, the individual providing input via means of the user interface or a control to vary the sound adaptation characteristic map, wherein the levels for the individual listening thresholds per frequency range of the different frequency ranges are used as minimum output levels in the sound adaptation characteristic map varied by the individual;
   wherein performing the adaptation of the second audio signal is repeated for different total volume levels; and wherein the method comprises storing the sound adaptation characteristic map per total volume level.

2. Method according to claim 1, wherein the first listening test and/or the adaptation is performed by using the audio devices selected by the individual and/or in the acoustic environment of the individual.

3. Method according to claim 1, wherein varying the sound adaptation characteristic map is performed by continuously adapting at least one dimension of the sound adaption characteristic map in order to smooth the resulting sound characteristic change over time and/or the sound pressure level differences over time.

4. Method according to claim 1, wherein the second audio signal is a test signal, a complex audio signal, a complex audio signal with a limited frequency range and/or a piece of music.

5. Method according to claim 1, wherein varying the sound adaptation characteristic map is performed for input levels above the level for the individual threshold and/or for levels below a level for limitation.

6. Method according to claim 5, wherein varying the sound adaptation characteristic map for input levels is at least 10 dB above the respective level for the individual threshold and/or at least 3 dB below the respective level for limitation.

7. Method according to claim 1, wherein playing the second audio signal is performed with the help of a multi-band compressor, wherein the multiband compressor post-processes the second audio signal with respect to the output levels in the different frequency ranges in dependence on the sound adaptation characteristic map.

8. Method according to claim 1, wherein the sound adaptation characteristic map is selected such that the same does not fall below a masking threshold, wherein the masking threshold depends on the individual listening threshold.

9. Method according to claim 1, wherein, when playing the plurality of first audio signals, a signal portion is added to the audio signals, which allows simulation of driving and/or ambient noise.

10. Method according to claim 1, wherein the second audio signal is an audio signal to be replayed and adaptation of the second audio signal is repeated during operation.

11. A non-transitory digital storage medium having a computer program stored thereon to perform the method for setting parameters for individual adaptation of an audio signal, the method comprising:
performing a first listening test with the following substeps:
playing a plurality of first audio signals with different levels and for different frequency ranges to output a plurality of first acoustic signals of different sound pressure levels in the different frequency ranges to an individual;
obtaining feedback per frequency range of the different frequency ranges from the individual, which of the plurality of first acoustic signals is above an individual listening threshold; and
using, per frequency range of the different frequency ranges, the lowest level of the different levels of the plurality of first audio signals for which feedback is available, which characterizes the associated first acoustic audio signal as an acoustic audio signal above the individual listening threshold, as a level for the individual listening threshold per frequency range of the different frequency ranges;
performing adaptation of a second audio signal with the following substeps:
playing the second audio signal according to a total volume level selected by the individual considering a sound adaptation characteristic map to output a post-processed second acoustic signal to the individual; and
varying the sound adaptation characteristic map by means of a user interface or a control until the individual indicates by interaction that no further variation of the sound adaptation characteristic map is desired;
wherein the varying the sound adaptation characteristic map is performed based on an interaction of the individual, the individual providing input via means of the user interface or a control to vary the sound adaptation characteristic map, wherein the sound adaptation characteristic map defines an individual boost and/or individual cut of the output level per input level for different frequency ranges, wherein the levels for the individual listening thresholds per frequency range of the different frequency ranges are used as minimum output levels in the sound adaptation characteristic map varied by the individual;
wherein performing the adaptation of the second audio signal is repeated for different total volume levels; and
wherein the method comprises storing the sound adaptation characteristic map per total volume level;
when said computer program is run by a computer.

12. Apparatus for setting parameters for individual adaptation of an audio signal, comprising:
an initial adaptation stage for defining levels for an individual listening threshold per frequency range of the different frequency ranges, comprising devices for:
playing a plurality of first audio signals with different levels and for different frequency ranges to output a plurality of first acoustic signals of different sound pressure levels in the different frequency ranges to an individual;
obtaining feedback per frequency range of the different frequency ranges from the individual, which of the plurality of first acoustic signals is above the individual listening threshold; and
wherein, per frequency range of the different frequency ranges, the lowest level of the different levels of the plurality of first audio signals for which feedback is available, which characterizes the associated first acoustic audio signal as an acoustic audio signal above the individual listening threshold, is used as the level for the individual listening thresholds per frequency range of the different frequency ranges;
a further adaptation stage for adapting a second audio signal, comprising devices for:
playing the second audio signal according to a total volume level selected by the individual considering a sound adaptation characteristic map to output a post-processed second acoustic signal to the individual; and
varying the sound adaptation characteristic map by means of a user interface or a control until the individual indicates by interaction that no further variation of the sound adaptation characteristic map is desired;
wherein the varying the sound adaptation characteristic map is performed based on an interaction of the individual, the individual providing input via means of the user interface or a control to vary the sound adaptation characteristic map, wherein the sound adaptation characteristic map defines an individual boost and/or individual cut of the output levels per input level for different frequency ranges; wherein the levels for the individual listening thresholds per frequency range of the different frequency ranges are used as minimum output levels in the sound adaptation characteristic map varied by the individual;
wherein performing the adaptation of the second audio signal is repeated for different total volume levels; and
wherein the method comprises storing the sound adaptation characteristic map per total volume level.

13. Apparatus according to claim 12, wherein the apparatus comprises a user interface for receiving the feedback and/or for varying the sound adaptation characteristic map; or
wherein the apparatus comprises a user interface for receiving the feedback and/or for varying the sound adaptation characteristic map and wherein the user interface comprises one or several controls for individual boost and/or for individual cut of the output levels in at least two frequency ranges or a two-dimensional sound adaptation map.

14. Apparatus according to claim 12, wherein the apparatus comprises a memory for storing the sound adaptation characteristic map.

15. Vehicle sound system comprising the apparatus according to claim 12.

* * * * *